United States Patent [19]
Humphrey et al.

[11] Patent Number: 5,567,722
[45] Date of Patent: Oct. 22, 1996

[54] CYANOGUANIDINES AS K-CHANNEL BLOCKERS

[75] Inventors: Stephen J. Humphrey; Kaushik D. Meisheri; James H. Ludens, all of Kalamazoo; Jackson B. Hester, Jr., Galesburg, all of Mich.

[73] Assignee: The Upjohn Company, Kalamazoo, Mich.

[21] Appl. No.: 384,562

[22] Filed: Feb. 6, 1995

Related U.S. Application Data

[63] Continuation of PCT/US93/06752, Jul. 21, 1993, continuation-in-part of Ser. No. 929,795, Aug. 13, 1992, abandoned.

[51] Int. Cl.$^6$ .................. C07D 213/75; A61K 31/44
[52] U.S. Cl. .............................. 514/353; 546/306
[58] Field of Search ..................... 546/306; 514/353

[56] References Cited

U.S. PATENT DOCUMENTS 4,057,636 11/1977 Petersen .................................. 546/306

FOREIGN PATENT DOCUMENTS 89-166119 6/1989 Japan ..................................... 546/306

OTHER PUBLICATIONS

Smallwood, JK, J. Card. Pharm., 12–:102–9 (1988).
Peterson HJ, J. Med. Chem., 21(8):773–781 (1978).
Robertson DW, et al., Annual Reports in Medicinal Chemistry 24, Ch 10, 91–100 (1989).
Petersen, *Journal of Medicinal Chemistry*, vol. 21, No. 8, 1978, pp. 773–781.

Primary Examiner—Zinna Northington Davis
Attorney, Agent, or Firm—Donald L. Corneglio

[57] ABSTRACT

Cyanoguanidine compounds of Formula I and its pharmaceutically acceptable acid addition salts

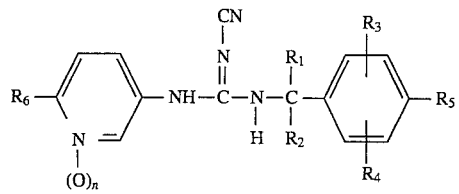

wherein $R_1$ is hydrogen or methyl;

$R_2$ is $C_1$–$C_6$ alkyl, $C_2$–$C_6$ alkenyl, $C_2$–$C_6$ alkynyl, $C_3$–$C_5$ cycloalkyl, $C_3$–$C_5$ cycloalkenyl hydroxy methyl, methoxy-$C_1$–$C_5$ alkyl, or $R_1$ and $R_2$ are combined to form a $C_3$–$C_6$ carbocyclic ring;

$R_3$ and $R_4$ are each independently selected to be hydrogen, $C_1$–$C_4$ alkyl, F, Cl, Br, I or $CF_3$;

$R_5$ is hydrogen, F or Cl;
$R_6$ is hydrogen, —$NH_2$, —$NHCH_3$, —$NHC_2H_5$, —NH-$CH(CH_3)_2$, —$N(CH_3)_2$, —$N(C_2H_5)_2$, $NH(CH_2)_m$—$OC_1$–$C_3$ alkyl (where m is 2 or 3), —NHC(O)$C_1$–$C_3$ alkyl, Cl or Br; and n is 0 or 1.

The compounds of Formula I are potassium channel blockers useful in the treatment of cardiovascular disorders such as congestive heart failure and hypertension and as a diuretic.

8 Claims, No Drawings

CYANOGUANIDINES AS K-CHANNEL BLOCKERS

CROSS-REFERENCE TO RELATED APPLICATIONS

This application is a continuation of PCT/US93/06752, filed 21 Jul. 1993, which was a continuation-in-part of U.S. Ser. No. 07/929,795, filed 13 Aug. 1992, abandoned.

BACKGROUND OF THE INVENTION

The present invention is directed toward cyanoguanidine compounds which are potassium channel blockers useful in the treatment of cardiovascular disorders such as congestive heart failure and hypertension. The cyanoguanidine compounds of this invention, unlike other cyanoguanidines, block potassium channel conduction in vascular smooth muscle and in ATP-sensitive potassium channels in apical membranes of the kidney.

It is known that $K^+$ channels are important for regulating potassium excretion by the kidney and it has been proposed that inhibition of ATP-sensitive $K^+$ channel conduction in apical cell membranes of the thick ascending limb of Henle's loop would reduce potassium recycling across the membrane and thus reduce sodium resorption via the $Na^+$-$2Cl^-$-$K^+$ co-transporter. It has also been proposed that inhibition of the ATP-sensitive $K^+$ channels of apical membranes in principal cells of the initial and cortical collecting tubule would reduce $K^+$ secretion, the primary source of urinary potassium. $K^+$ channel antagonist activities necessary to produce the observed eukalemic natriuresis have been documented in the rat kidney.

The subject compounds are effective blockers for the ATP-sensitive potassium channels of the thick ascending limb of Henle's loop and the principal cells of the initial and cortical collecting tubules of the kidney. This activity results in an enhanced urinary excretion of sodium and water without enhanced potassium excretion. This provides a useful diuresis which is not complicated by an undesirable reduction in plasma potassium levels or hypokalemia.

Thus, the subject series of cyanoguanidines, although very closely related to the $K^+$ channel agonist pinacidil and related compounds, are potent $K^+$ channel antagonists.

INFORMATION DISCLOSURE STATEMENT

U.S. Pat. No. 4,057,636 discloses pyridylguanidine compounds structurally similar to the subject compounds except that the subject compounds have a branched methylene linking group to a phenyl which can be optionally substituted. Surprisingly, the subject compounds are potassium channel blockers whereas the compounds of 4,057,636 are potassium channel openers.

Pyridine N-oxide and pinacidil and its related pyridylcyanoguanidines are a class of compounds structurally related to the subject invention. Articles disclosing these compounds are as follows: Smallwood, JK, J. Card. Pharm., 12:102–9 (1988): and Peterson, HJ, J. Med. Chem., 21(8):773– 81 (1978).

Other publications include, JP 166119, published Jan. 2, 1991, discloses cyanoguanidine derivatives have a branched alkyl group at the C-1 position but no phenyl group attached thereto. GB 055209, Dec. 20, 1974, Leo Pharmaceutical, discloses N-cyano-N'-pyridyl guanidine as hypotensives.

European Patent Application 92104287.5 discloses compounds having a pyridine N-oxide and amine substitutions although not linked to a phenyl.

DE-A-3005786 discloses structurally different cyanoguanidines having diuretic activity but no enhanced sodium excretion is mentioned.

The state of the art on potassium channel mechanisms and pinacidil is discussed in Annual Reports in Medicinal Chemistry, Robertson DW, et al., 24, Ch 10, 91–100 (1989).

SUMMARY OF THE INVENTION

In one aspect the present invention is a compound of Formula I and its pharmaceutically acceptable acid addition salts

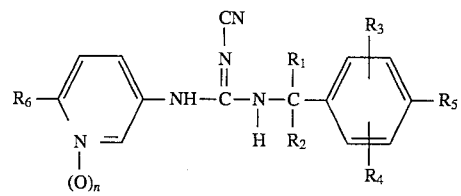

wherein
$R_1$ is hydrogen or methyl;
$R_2$ is $C_1$–$C_6$ alkyl, $C_2$–$C_6$ alkenyl, $C_2$–$C_6$ alkynyl, $C_3$–$C_5$ cycloalkyl, $C_3$–$C_5$ cycloalkenyl hydroxymethyl, methoxy-$C_1$–$C_5$ alkyl, or $R_1$ and $R_2$ are combined to form a $C_3$–$C_6$ carbocyclic ring;
$R_3$ and $R_4$ are each independently selected to be hydrogen, $C_1$–$C_4$ alkyl, F, Cl, Br, I or $CF_3$;
$R_5$ is hydrogen, F or Cl.
$R_6$ is hydrogen, $-NH_2$, $-NHCH_3$, $-NHC_2H_5$, $-NHCH(CH_3)_2$, $-N(CH_3)_2$, $-N(C_2H_5)_2$, $-NH(CH_2)_m-$ $OC_1$–$C_3$alkyl (where m is 2 or 3), $-NHC(O)C_1$–$C_3$alkyl, Cl or Br; and n is 0 or 1.

In another aspect, the subject invention is useful as a potassium channel blocker and can be used in the treatment of cardiovascular disorders such as congestive heart failure, hypertension and shock.

DETAILED DESCRIPTION OF THE INVENTION

The present invention is directed toward compounds of Formula I and its pharmaceutically acceptable acid addition salts, as structurally depicted above. The compounds of Formula I include both enantiomers as well as salts and tautomeric forms.

It has been found that the 3-pyridyl and phenyl substituents are required for activity. At least one substituent must be present on the benzylic carbon and when only one alkyl substituent is present the activity resides with the (R) enantiomer. Particularly preferred are compounds with small cycloalkyl, alkyl or $R_1R_2$ carbocyclic substituents on the benzylic carbon and with a 3-chloro or 3-fluoro substituent on the phenyl ring.

Pharmaceutically acceptable acid addition salts of the Formula I, may be chosen from the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate.

The carbon content of various hydrocarbon-containing moieties is indicated by a prefix designating the minimum and maximum number of carbon atoms in the moiety, i.e., the prefix $C_i$–$C_j$ indicates a carbon atom's content of the integer "i" to the integer "j" carbon atoms, inclusive. For example, $C_1$–$C_3$ alkyl refers to alkyl of 1–3 carbon atoms, inclusive, or methyl, ethyl, propyl, and isopropyl, and isomeric forms thereof.

$C_3$–$C_5$ cycloalkyl is cyclopropane, cyclobutane, cyclopentane and isomeric forms thereof.

A "$C_3$–$C_6$ carbocyclic ring" means cyclopropyl, cyclobutyl, cyclopentyl, cyclohexyl, cyclobutenyl, cyclopentenyl or cyclohexenyl.

Preferred compounds of Formula I are:

(R) N"-Cyano-N-(3-pyridyl)-N'-(1-phenylpropyl)guanidine;

N"-Cyano-N-(3-pyridyl)-N'-(1-phenylcyclobutyl)guanidine;

N"-Cyano-N-(3-pyridyl)-N'-[1 -(3-chlorophenylpropyl] guanidine;

N"-Cyano-N-(3-pyridyl)-N'-phenylcyclopropylmethylguanidine;

N"-Cyano-N-(3-pyridyl)-N'-[1-(3-chlorophenyl)cyclobutyl]guanidine;

(R)-N"-Cyano-N-(6-amino-3-pyridyl)-N'-(1-phenylpropyl)guanidine; and

N"-Cyano-N-(6-amino-3-pyridyl)-N'-(1-phenylcyclobutyl)guanidine.

The compounds of Formula I will thus be useful for treating cardiovascular disorders such as congestive heart failure and forms of hypertension that can benefit from a reduction in plasma fluid volume. In addition, the compounds of this invention, by virtue of their potassium channel blocking activity, will be useful for preventing the undesirable increase in plasma renin activity that might be expected to result from a reduction of plasma fluid volume or from reductions in blood pressure by other co-administered antihypertensive agents. This activity will enhance the antihypertensive activities of both agents.

This invention thus contemplates the co-administration of compounds of Formula I with other antihypertensive agents such as the ACE inhibitors, the β-adrenergic blockers, the $\alpha_1$-adrenergic blockers, the $\alpha_2$-adrenergic agonists, calcium channel blockers, and other vasodilators such as the nitrates and hydralazine, etc. In addition, the compounds of Formula I are useful for their antiarrhythmic activity and their ability to antagonize overdoses of potassium channel agonists, to prevent excessive hair growth, to increase insulin release, to treat shock, to control reflex hyperemia and to reduce body weight.

The enantiomers of the compounds of Formula I in which $R_1$ and $R_2$ are different are considered to be important variations of this invention. When $R_1$ is hydrogen and $R_2$ is alkyl the preferred enantiomer has the (R) absolute configuration. Also important are the pharmacologically acceptable acid addition salts, the pharmaceutical preparations for oral, transdermal and parenteral administration and the novel chemical intermediates and processes for the preparation of the compounds of Formula I.

The compounds can be administered intravenously, intramuscularly, topically, transdermally such as by skin patches, bucally, suppositorally or orally to man or other animals.

The compositions of the present invention can be presented for administration to humans and animals in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions.

For oral administration, either solid or fluid unit dosage forms can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration, fluid unit dosage forms can be prepared utilizing the compound and a sterile vehicle. In preparing solutions the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The dry lyophilized powder can then be sealed in the vial and reconstituted prior to use.

As diuretic agents the compounds of Formula I can be used in unit dosages of 1 to 1000 mg in oral or injectable preparations.

CHEMISTRY

The subject compounds were prepared by the successive reaction of two amines with diphenyl cyanocarbonimidate (i).

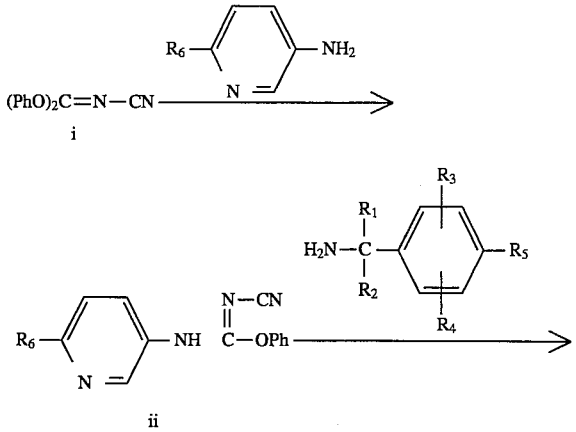

FORMULA I

The first reaction was normally carried out with one equivalent of the less reactive amine in $Et_2O$ or ethylene glycol dimethyl ether at 25° C. In some cases, however, this procedure was unsuccessful and other solvents or conditions were required. When $R_6$ was chlorine in the above reaction, for example, it was necessary to warm the mixture of i and the amine to 120° C. without solvent to complete the reaction. In the second step the second amine was usually allowed to react with ii in refluxing isopropanol or dioxane. This reaction required either two equivalents of the amine (Procedure A, explained below in Example 1) or one equivalent of the amine when an excess of N-methylmorpholine was employed (Procedure B, explained below in Example 2). Several variations in these procedures were required for the preparation of specific compounds, explained in Table I and II footnotes.

During the preparation of Example 4 by Procedure B, a byproduct, apparently resulting from cyclization and elimination of cyanamide, was obtained. This cyclization was avoided in the preparation of Example 27 by allowing the reaction to proceed at ambient temperature.

TABLE I

Physical and Analytical Data for the Cyanoguanidines of Formula I where $R_6$ is hydrogen and n is zero.

| Example # | $R^1$ | $R^2$ | Z | Proc. | mp, °C. | Recryst. Solvent |
|---|---|---|---|---|---|---|
| 1[m] | H | $CH_3$ | Ph | A | 185–187 | $MeOH-CH_2Cl_2-EtOAc$ |
| 2 | H | $C_2H_5$ | Ph | B | 155–156 | MeOH—EtOAc |
| 3 | $-CH_2CH=CH-CH_2$ | | Ph | C | 155.5–157 | EtOAc |
| 4[q] | H | $CH_2OH$ | Ph | — | 175–176 | MeOH—EtOAc-hexane |
| 5 | H | $C_3H_7$ | 3ClPh | — | 153–155 | MeOH—EtOAc-hexane |
| 6 | $-CH_2-CH_2-CH_2-$ | | Ph | — | 159–160 | MeOH—EtOAc-hexane |
| 7[o] | H | $CH_3$ | Ph | — | 181–182 | $MeOH-CH_2Cl_2-(CH_3)_2CO$ |
| 8[n] | H | $CH_3$ | Ph | A[b] | 185–187 | $MeOH-CH_2Cl_2-(CH_3)_2CO$ |
| 9 | $CH_3$ | $CH_3$ | Ph | A[a] | 163–165 | EtOAc |
| 10 | $-CH_2(CH_2)_3CH_2-$ | | Ph | A[c,j] | 204–205 | $CH_2Cl_2-MeOH-EtOAc$ |
| 11 | $-CH_2(CH_2)_2CH_2-$ | | Ph | A[c,d,j] | 169–171 | EtOAc |
| 12 | H | $CH(CH_3)_2$ | Ph | B[e] | 169 | MeOH—EtOAc |
| 13 | H | $C(CH_3)_3$ | Ph | B[e] | 149–151 | $CH_2Cl_2-EtOAc$ |
| 14 | H | $CH_3$ | $2CH_3Ph$ | B | 220 | MeOH |
| 15 | H | $CH_3$ | $3CH_3Ph$ | B[g] | 137 | EtOAc-hexane |
| 16 | H | $CH_2OCH_3$ | Ph | B[h] | 163–164 | $MeOH-CH_2Cl_2$-hexane |
| 17 | H | $CH(CH_2)_2$ | Ph | B[f] | 147–148 | $CH_2Cl_2-EtOAc$ |
| 18 | H | $CH(CH_2)_4$ | Ph | B[i] | 132–133 | $CH_2Cl_2-EtOAc$ |
| 19 | H | $CH(CH_2)_3$ | Ph | B[i] | 147–148 | MeOH—EtOAc |
| 20[p] | H | $C_2H_5$ | Ph | B[i] | 144–145 | MeOH—EtOAc-hexane |
| 21 | H | $CH_3$ | $3CF_3Ph$ | B[i] | 179.5–180.5 | MeOH—EtOAc-hexane |
| 22[r] | H | $C_2H_5$ | Ph | B[i] | 144.5–147 | MeOH—EtOAc-hexane |
| 23 | H | $CH_3$ | 3,4DiClPh | B[j,l] | 160–162 | $CH_3CN$ |
| 24 | H | $CH_3$ | 2,5DiClPh | B[j] | 210–211 | MeOH—EtOAc |
| 25 | H | $CH_3$ | 3ClPh | B[l] | 176–177.5 | EtOAc |
| 26 | H | $CH_3$ | 2ClPh | B[l] | 223–224 | MeOH—EtOH |
| 27[s] | H | $CH_2OH$ | Ph | B[k] | 176–177 | MeOH[c] |
| 28 | H | $(CH_2)_2CH_3$ | Ph | B | 157–159 | MeOH—EtOAc |

TABLE II

Physical and Analytical Data for Cyanoguanidines of Formula I as shown in Table I (n = 0 except where indicated).

| Example # | $R_6$ | $R_1$ | $R_2$ | Z | Proc. | mp, °C. | Recryst. Solvent |
|---|---|---|---|---|---|---|---|
| 29 | MeNH | $CH_3$ | H | Ph | C[t] | 123–126 | MeOH—EtOAc |
| 30 | MeCONH | $C_2H_5$ | H | Ph | C[v] | 193.5–194.5 | MeOH—EtOAc Cyclohexane |
| 31 | H | $-CH_2CH_2CH_2-$ | | 3Br—Ph | C[w] | 207.5–209 | MeOH—EtOAc |
| 32 | H | $-CH_2CH_2CH_2-$ | | 3Cl,2F—Ph | D | 219–220 | MeOH—EtOAc |
| 33[q,x] | $Et_2N$ | $CH_3$ | H | Ph | C[t] | 159–160.5 | MeOH—EtOAc |
| 34[q] | Cl | $CH_3$ | H | Ph | C[d] | 133–134 | $Me_2CHOH-Me_3COMe$ |
| 35[q] | $Me_2N$ | $CH_3$ | H | Ph | C[y] | 128–129 | $Me_2CHOH$ |
| 36[z] | $NH_2$ | $CH_3$ | H | Ph | C[aa] | 93(dec) | EtOAc-hexane |
| 37[s,bb] | $Me_2N$ | $CH_2OH$ | H | Ph | C[cc] | 98–99 | $MeOH-Me_3COMe$ pentane |
| 38 | H | $C_2H_5$ | H | 3F—Ph | C[d] | 146–147 | EtOAc |
| 39 | H | $C_2H_5$ | H | 3Br—Ph | C | 154–155 | $CH_3CN$ |
| 40 | H | $CH_3$ | H | 3,5di-F—Ph | C[dd] | 187–188 | $CH_3CN$ |
| 41 | H | $C_2H_5$ | H | 3I—Ph | — | 174–176 | $CH_3CN$ |
| 42 | H | $-CH_2CH_2CH_2-$ | | 3F—Ph | D[aa] | 167–168 | $CH_3CN$ |
| 43 | H | $C_2H_5$ | H | 2F—Ph | D | 171–172 | $CH_3CN$ |

TABLE II-continued

Physical and Analytical Data for Cyanoguanidines of Formula I as shown in Table I (n = 0 except where indicated).

| Example # | $R_6$ | $R_1$ | $R_2$ | Z | Proc. | mp, °C. | Recryst. Solvent |
|---|---|---|---|---|---|---|---|
| 44[q,cc] | $NH_2$ | $C_2H_5$ | H | Ph | D | 177.5–179.5 | $CH_3CN$ |
| 45 | H | $-CH_2CH_2CH_2-$ | | 3Cl—Ph | D | 201–202 | $CH_3CN$ |
| 46[cc] | $NH_2$ | $-CH_2CH_2CH_2-$ | | Ph | D[ff] | 135(dec) | $CH_3CN$ |
| 47 | $NH_2$ | $-CH_2CH_2CH_2-$ | | 3F—Ph | D[ff] | 194–195 | MeOH—EtOAc |
| 48 | H | $-CH_2CH_2CH_2-$ | | 2,3Di,F—Ph | D | 204–205 | MeOH |
| 49 | $NH_2$ | $-CH_2CH_2CH_2-$ | | 2,3Di,F—Ph | D[ff] | 219–220 | $CH_3CN$ |
| 50 | H | $CH_3$ | H | 3F—Ph | C | 157–158 | MeOH—EtOAc-hexane |
| 51[z] | H | $-CH_2CH_2CH_2-$ | | Ph | C[gg] | 159–160 | MeOH—EtOAc-hexane |
| 52 | H | $C_2H_5$ | H | 3Cl—Ph | C | 153–155 | MeOH—EtOAc-hexane |
| 53[q] | $Me_2NH$ | $C_2H_5$ | H | Ph | C | 109–111 | MeOH—EtOAc-hexane |
| 54[kk] | H | $C_2H_5$ | H | Ph | — | 187–188 | $CH_3CN$ |
| 55[q,bb,kk] | H | $CH_3$ | H | Ph | — | 195–197 | MeOH—$CH_3CN$ |
| 56[q] | EtNH | $CH_3$ | H | Ph | C | 124–125 | EtOAc-hexane |
| 57[q] | $MeO(CH_2)_3NH$ | $CH_3$ | H | Ph | C[hh] | 140–145 | $CHCl_3$—$Et_2O$-hexane |
| 58 | H | $CH_3$ | H | 2,3di-F—Ph | C[ii] | 177–178 | $(CH_3)_2CO$-hexane |
| 59[q] | $Me_2CHNH$ | $CH_3$ | H | Ph | C[jj] | 115–116 | EtOAc-hexane |
| 60 | H | $C_2H_5$ | H | 2,5Di-F—Ph | D | 184–185 | MeOH—EtOAc |
| 61 | H | $C_2H_5$ | H | 2,6Di-F—Ph | D | 214–215 | MeOH |
| 62 | H | $C_2H_5$ | H | 3,4Di-F—Ph | D | 146–147 | MeOH—EtOAc-hexane |
| 63 | H | $-CH_2CH_2-$ | | Ph | C[gg] | 185–186 | MeOH—EtOAc-hexane |

Notes for Table I and II.
[a]Product purified by silica gel chromatography with EtOAc.
[b]Product purified by silica gel chromatography with 3–10% MeOH—$CHCl_3$.
[c]Reaction mixture refluxed for 18–24 hours.
[d]Product purified by silica gel chromatography with 2–5% MeOH—$CHCl_3$.
[e]Product purified by silica gel chromatography with 100% hexane - 100% EtOAc.
[f]Product purified by silica gel chromatography with 1–5% MeOH/0.1–0.5% $NH_4OH/CHCl_3$.
[g]Product purified by silica gel chromatography with 1–4% MeOH/0.1–0.4% $NH_4OH/CHCl_3$.
[h]The crude product was contaminated which resulted from an impure sample of the amine. Compound 16 was purified by silica gel chromatography first with 1–5% MeOH/0.1–0.5% $NH_4OH/CHCl_3$ and then with a second high performance column with 1–3% MeOH—$CHCl_3$.
[i]Product purified by silica gel chromatography with 1–3% MeOH—$CHCl_3$.
[j]For preparation of the amine see Experimental Section.
[k]Reaction mixture was kept at ambient temperature for 3 days; the product began to crystallize from the mixture after 24 hours.
[l]This preparation utilized 2.6 to 2.8 equivalents of N-methylmorpholine.
[m](R) Enantiomer, $[\alpha]_D^{24}$ −80° (c 1.03, EtOH).
[n](S) Enantiomer, $[\alpha]_D^{24}$ +78° (c 0.995, EtOH).
[o]Racemate.
[p](S) Enantiomer, $[\alpha]_D^{24}$ +39° (c 0.993, EtOH).
[q](R) Enantiomer.
[r](R) Enantiomer, $[\alpha]_D^{24}$ −39° (c 1.0043, EtOH).
[s](S) Enantiomer.
[t]Product purified by silica gel chromatography with 1% MeOH - 0.1% $NH_4OH$—$CH_2Cl_2$.
[u]Hemifumarate salt, ethyl acetate solvate.
[v]Product purified by silica gel chromatography with 1 to 3% MeOH - 0.1 to 0.3% $NH_4OH$—$CH_2Cl_2$.
[w]Product purified by silica gel chromatography with 2% MeOH - 0.2% $NH_4OH$—$CH_2Cl_2$.
[x]Methanesulfonic acid salt (1:1)
[y]Product purified by silica gel chromatography with 20–30% $EtOAc/CH_2Cl_2$.
[z]Ethyl acetate solvate
[aa]Product purified by silica gel chromatography with 5% MeOH - 0.25% $NH_4OH$—$CHCl_3$.
[bb]Hydrate
[cc]Reaction mixture heated at 60° C. for 48 hours; product purified by silica gel chromatography with 7.5% MeOH - 0.35% $NH_4OH$—$CHCl_3$.
[dd]Product purified by silica gel chromatography with 3.5% MeOH - 0.15% $NH_4OH$—$CHCl_3$.
[ee]Acetonitrile solvate
[ff]Product purified by silica gel chromatography with 5% MeOH—$CHCl_3$.
[gg]Product purified by silica gel chromatography with 1–4% $MeOH/CHCl_3$.
[hh]Product purified by silica gel chromatography with mixtures of ethyl acetate-hexane containing 20–100% EtOAc.
[ii]Product purified by silica gel chromatography with 0–8% MeOH—$CHCl_3$.
[jj]Product purified by silica gel chromatography with 1–5% MeOH—$CHCl_3$.
[kk]Pyridine N-oxide (n = 1).

Compounds of the subject invention were tested for diuretic effect as well as potassium channel blocking activity.

The results for potassium channel blocking were obtained by using isolated rabbit mesenteric artery (RMA) procedures. Norepinephrine (5 μM) was used to contract the RMA rings twice, with an hour separating the two contractions. During this hour the tissues equilibrated in physiological salt solution at a resting tension of 1 gram. Upon the plateau of the second contraction 1 μM pinacidil was added to all tissues and the resulting relaxation time course was studied for thirty minutes. Pinacidil at this concentration has been shown to produce maximal $K^+$ channel dependent vasodilation in the system. By studying the ability of the test compounds to inhibit this pinacidil-induced relaxation, the degree of potassium antagonism could be determined. The compounds were applied to the tissues for one hour between the two contractions and the pinacidil-induced relaxation was studied in the continuing presence of the compounds. Thus, the total time of pretreatment with the test compound was 75 minutes before the addition of pinacidil. Only one tissue was used per concentration of each compound, and in the case of no relaxation, the tissues were shown to be capable of relaxation by known vasodilators. The compounds were tested at 5 μM. The inhibitory effect of a compound was measured as percent inhibition of pinacidil relaxation at 15 minutes in comparison with the control.

Data for K$^+$ channel antagonist activity on rabbit mesenteric artery (RMA) and natriuretic efficacy after intraparenteral (IP) administration to rats are collected in Tables III and IV. It was known, for example, that a compound where both methyl groups on the benzylic carbon of Example 9 had been removed was a weak PCO rather than a K$^+$ channel antagonist. Similarly a compound in which the phenyl was attached directly to the guanidine nitrogen was also a K$^+$ channel agonist. Example 9 in which the phenyl ring was separated from the guanidine nitrogen by one additional methylene had also been found to have poor activity in both the diuretic and the K$^+$ channel antagonist assays.

The diuretic activity was determined in female Harlan Sprague-Dawley rats weighing 200 to 230 grams that were fasted 15 hours overnight, and then were deprived of both food and water for an additional hour prior to dosing. Tables III and IV show the measurement of net increase (above control) in urinary Na$^+$ excretion (μEq) for a 5 hour test period divided by the total of the three drug doses (mg/kg) administered IP in the diuretic screen. It approximates the area under the dose response curve. The vehicle was 20% dimethylacetamide (DMA; v/v) in a pH 7.4 phosphate buffer (0.58% Na$_2$HPO$_4$ and 0.13% NaH$_2$PO$_4$.H$_2$O). Sufficient drug was suspended in 1 to 2 ml of this vehicle to deliver doses of 1.0 to 30 mg/kg in a volume of 0.5 ml (2–4 rats/dose). At least 2 vehicle control rats, and, for most tests, 2 standard diuretic treated rats were included in each experiment. Standards used as comparators included the K$^+$ retaining diuretic amiloride and the K$^+$ wasting diuretics furosemide, hydrochlorothiazide and metolazone.

Following their IP doses, the rats' urinary bladders were gently compressed to eliminate all pretreatment urine, and two identically treated rats were placed in a stainless steel metabolism cage equipped with a graduated test tube to collect voided urine. At 2 and 5 hours post treatment, the rats' bladders were again compressed, the volume of urine excreted by the pair of rats was recorded, and aliquots of urine were retained for analysis of Na$^+$ and K$^+$ concentrations with a NOVA-13 selective ion analyzer. Following the 5 hour urine collection, the rats were returned to their stock cages, and at least 1 week of recovery was allowed between a maximum of 3 diuretic tests.

The electrolyte concentrations detected in these urine samples were manually multiplied by their respective volumes to determine total milliequivalent (mEq) excretion of Na$^+$ and K$^+$ per pair of rats, and the results obtained with multiple racks per drug treatment were averaged. Increases in urinary Na$^+$ excretion of 50% or more above the pooled control tests were regarded as reflecting activity.

TABLE III

Natriuretic and Vascular Potassium Channel Antagonist Activities for the Compounds in Table I.

| Compound # | RMA K$^+$ Channel Antagonism % I at 5 μM$^a$ | 5 h Net Natriuretic Efficacy (μEq Na$^+$/mg/kg)$^i$ |
|---|---|---|
| Control* | 0.0 ± 0.0 (2)$^b$ | 0.4 |
| Pinacidil** | 0.0 (1) | −60$^j$ |
| 1 | 86.3 ± 5.0 (6)$^c$ | 51.7 |
| 2 | 78.8 ± 3.9 (3)$^g$ | 38.4 |
| 3 | 91.0 | 57 |
| 4 | 2.6 ± 1.7 (2) | 20 |
| 7 | 65.3 ± 10.2 (5) | 29.4 |
| 8 | 22.1 ± 21.2 (3) | 1.9 |
| 9 | 89.5 ± 3.6 (6) | 10 |
| 10 | 85.5 ± 2.2 (3) | 13.0 |
| 11 | 90.4 ± 2.3 (2)$^f$ | 46.8 |
| 12 | 85.5 ± 0.6 (2)$^d$ | 35 |
| 13 | 83.2 ± 12.0 (3)$^e$ | 28 |
| 14 | 58.7 ± 8.3 (3) | 21.2 |
| 15 | 82.0 ± 3.9 (2) | 10.0 |
| 16 | 51.1 ± 11.6 (3) | 19 |
| 17 | 93.3 ± 2.2 (3) | 42.2 |
| 18 | 88.1 ± 2.0 (2) | 2.0 |
| 19 | 96.0 ± 2.1 (2) | 19 |
| 20 | 13.9 ± 7.2 (3) | −3 |
| 21 | 85.3 ± 3.2 (5) | 9 |
| 22 | 89.0 ± 3.2 (3)$^h$ | 45 |
| 23 | 90.8 ± 2.8 (2) | 13.6 |
| 24 | 86.9 ± 4.0 (2) | 12 |
| 25 | 89.9 ± 0.1 (2) | 38.8 |
| 26 | 74.7 ± 2.7 (2) | 6.4 |
| 27 | 92.5 ± 3.1 (3) | 47 |
| 28 | 85.2 ± 4.8 (2) | 9.8 |

Notes for Table III
*Not a compound of the subject invention; X is CH, R$_1$ and R$_2$ are H and Z is CH(Ph)$_2$.
**Not a compound of the subject invention.
$^a$This is a measure of a compound's ability to inhibit the relaxation of norepinephrine (5 μM) contracted rabbit mesenteric artery rings by pinacidil (1 μM). It is expressed as percent inhibition (mean ± sem) at an inhibitor concentration of 5 μM. Compounds with 65% or greater inhibition at 5 μM are considered to be active, with 20–65% inhibition moderately active and with less than 20% inhibition inactive.
$^b$Number of mesenteric rings used for the determination shown in parentheses for Examples 1–28.
$^c$Percent inhibition was 88.9 ± 11.2 (2) at 2.5 μM and 17.1 ± 11.9 (5) at 1 μM.
$^d$Percent inhibition was 78.2 ± 1.9 (2) at 1 μM and 43.6 ± 24.3 (2) at 0.5 μM.
$^e$Percent inhibition was 82.0 ± 1.8 (2) at 0.5 μM.
$^f$Percent inhibition was 78.8 ± 4.4 (4) at 0.5 μM.
$^g$Percent inhibition was 25.6 ± 17.2 (2) at 1 μM.
$^h$Percent inhibition was 81.5 ± 5.9 (6) at 0.5 μM, 52.0 ± 10 (3) at 0.25 μM and 5.0 ± 2.0 (4) at 0.1 μM
$^i$This represents the net increase (above control) in urinary Na$^+$ excretion (μEq) for the 5 hour test period divided by the total of the three drug doses (mg/kg) administered IP in the stage II diuretic screen in rats. It approximates the area under the dose response curve.
$^j$Antidiuresis seen with 5 mg/kg oral dosage. Similar responses have been obtained with IP and IV administration.

TABLE IV

Natriuretic and Vascular Potassium Channel Antagonist Activities for the Compounds of Table II.

| Compound # | RMA K$^+$ Channel Antagonism % I (conc. μM)$^{a,c}$ | 5 h Net Natriuretic Efficacy (μEq Na$^+$/mg/kg)$^d$ |
|---|---|---|
| 29 | 63.4(5) | 21 |
| 30 | 0.0(5) | 13 |
| 31 | 50(0.05) | 40 |
| 32 | 66(0.05) | 24 |
| 33 | 10.8(5) | 17$^b$ |
| 34 | 49.5(1) | 27 |
| 35 | 10.6(5) | 27 |
| 36 | 66.5(5) | 13 |
| 37 | 6.6(5) | 21 |

TABLE IV-continued

Natriuretic and Vascular Potassium Channel Antagonist
Activities for the Compounds of Table II.

| Compound # | RMA K$^+$ Channel Antagonism % I (conc. μM)$^{a,c}$ | 5 h Net Natriuretic Efficacy (μEq Na$^+$/mg/kg)$^d$ |
|---|---|---|
| 38 | 68.6(0.5) | 39 |
| 39 | 87.2(0.5) | 29 |
| 40 | 55.5(0.5) | 32 |
| 41 | 90.1(5) | 12 |
| 42 | 50(0.05) | 70 |
| 43 | 30(0.05) | 48 |
| 44 | 60(5) | 60 |
| 45 | 91(0.05) | 52 |
| 46 | 45(0.5) | 81 |
| 47 | 79(0.05) | 47 |
| 48 | 45(0.05) | 33 |
| 50 | 94.6(5) | 37 |
| 51 | 82.9(0.5) | 57 |
| 52 | 94.0(0.5) | 26 |
| 53 | 4.1(5) | 31 |
| 54 | 15.4(5) | 16 |
| 55 | 16.3(5) | 27 |
| 56 | 19.1(5) | 29 |
| 57 | 7.8(5) | 16 |
| 58 | 92.1(0.5) | 55 |
| 59 | 8.5(5) | 20 |
| 60 | — | 35 |
| 61 | — | 15 |
| 63 | 86.0(5) | 30 |

Notes for Table IV
$^a$Lowest inhibitor concentration (μM) that gave greater than 20% inhibition or lowest concentration tested.
$^b$Administered orally.
$^c$See note a., Table III.
$^d$See note i, Table III.

Tables III and IV show that the compounds of the invention have good potassium channel antagonist activity as well as natriuretic activity.

EXAMPLE 1

(R)-N"-Cyano-N-(3-pyridyl)-N'-(1-phenyl)ethylguanidine (1). Procedure A.

A stirred mixture of N-(3-pyridyl)-N'-cyano-O-phenylisourea (see, Example 5 for procedure) (8.00 g, 0.336 mmol), (R)-α-methylbenzylamine (10.8 mL, 0.0835 mol) and isopropanol (53.3 mL) was refluxed, under nitrogen, for 4 hours. The reaction was complete by TLC with 10% MeOH-1% NH$_4$OH-CHCl$_3$. The mixture was concentrated in vacuo. The residue was mixed with EtOAc several times with concentration after each addition; the resulting solid was triturated with hot EtOAc, collected by filtration and recrystallized from MeOH-CH$_2$Cl$_2$-EtOAc to give 6.6 g of product: mp 185°–187° C.

EXAMPLE 2

N"-Cyano-N-(3-pyridyl)-N'-(1-phenyl)propylguanidine (2). Procedure B.

A stirred mixture of N-(3-pyridyl)-N'-cyano-O-phenylisourea (see, Example 5 for procedure) (13.93 g, 0.05836 mol), 1-phenylpropylamine (8.68 g, 0.0642 mol), N-methylmorpholine (139 mL) and isopropanol (92.9 mL) was refluxed, under nitrogen, for 18 hours. The reaction was complete by TLC with 10% MeOH-1% NH$_4$OH-CHCl$_3$. Concentration of the reaction mixture gave a residue that was mixed with EtOAc and concentrated several times until the product crystallized. The solid was boiled twice with small portions of EtOAc; each time the mixture was cooled and the liquid decanted. The resulting solid was crystallized from MeOH-EtOAc to give 7.87 g (43.8%) of product: mp 155°–156° C.

EXAMPLE 3

N"-Cyano-N'-(1-phenylcyclopent-3-enyl)-N-(3-pyridyl)guanidine (3).

Step 1: 4-Cyano-4-phenylcyclopentene

A modification of the method of Fayter et al. (Fayter, R. G., Jr., White, J. F. and E. G. Harris, U.S. Pat. No. 4,252,739 (1981)), was used for this preparation.

To a N$_2$ covered, mechanically stirred solution of 4.93 ml (42.6 mmol) of phenylacetonitrile in 85 ml of CH$_2$Cl$_2$ was added 4.94 ml (46.9 mmol) of cis-1,4 dichloro-2-butene followed by 0.86 g (2.1 mmol) of Aliquat 336. There was then added 5.3 g (85.3 mmol) of powdered KOH in portions over 2.25 hours. A cold water bath was used to control a slight exotherm and keep the reaction temperature at about 25° C. during the addition. The reaction was stirred at room temperature for 1 hour and then heated in an oil bath at 55°–60° C. (reflux) for 1 hour. After allowing the reaction to cool, there was added 42 ml of H$_2$O dropwise over 6 minutes. The mixture was transferred to a separatory funnel and mixed well. The aqueous fraction was separated and washed with Et$_2$O. The combined organic fractions were dried over MgSO$_4$ and concentrated in vacuo. The residue was distilled under reduced pressure and a single fraction was collected, 5.39 g, b.p. 62°–86° C. (0.05 mm Hg). This fraction was combined with 4.77 g of material from a previous run and heated neat under N$_2$ in an oil bath at 200° C. for 30 minutes and then allowed to cool. The residue was chromatographed in two portions over silica gel (1% EtOAc: hexane) to yield 6.0 g of 4-Cyano-4-phenylcyclopentene.

Step 2: 4-Phenyl-4-Cyclopentenecarboxylic acid.

To a N$_2$ covered suspension of 0.927 g (5.48 mmol) of the product from Step 1 in ml of ethylene glycol was added 0.92 g of KOH pellets and the mixture was heated at 205° C. in an oil bath. After heating for 3.25 hours, the reaction mixture (now a solution) was allowed to cool, diluted with 10 ml of H$_2$O and washed once with Et$_2$O. The aqueous fraction was cooled in an ice bath and acidified with about 7 ml of 2.5 N HCl. A crystalline solid precipitated and after purging the residual Et$_2$O with N$_2$, was collected on a filter. Recrystallization from EtOAc: cyclohexane yielded 0.535 g, m.p. 123.5°–125.5° C. (51.8%) and 0.141 g, m.p. 122°–124° C. (13.7%) of the titled product.

Step 3: 4-Phenyl-4-cyclopentenyl isocyanate.

To a N$_2$ covered solution of 2.0 g (10.6 mmol) of the product from Step 2 in 40 ml of toluene was added 2.2 ml (15.9 mmol) of triethylamine followed by 3.4 ml (15.9 mmol) of diphenylphosphorylazide. After heating in an oil bath at 90° C. for 55 minutes. The reaction was allowed to cool and concentrated in vacuo. The residue was partitioned between 150 ml of 1:1 Et$_2$O: hexane and 20 ml of pH 7 phosphate buffer. The aqueous layer was separated and washed once with 1:1 Et$_2$O: hexane. The combined organic fractions were washed with brine, dried over MgSO$_4$ and concentrated in vacuo. The residue was chromatographed over 50 ml of silica gel (1% EtOAc: hexane) to yield 1.46 g (74.3%) of the titled product.

Step 4: 4-Amino-4-phenylcyclopentene, hydrochloride.

To a N₂ covered solution of 1.46 g (7.9 mmol) of the product from Step 3 in 30 ml of the THF was added 5.11 ml (7.9 mmol) of 40% (1.54M) aqueous tetrabutylammonium hydroxide. After stirring at room temperature for 24 hours, the reaction mixture was concentrated in vacuo. The residue was partitioned between 250 ml of 1:1 Et₂O: hexane and 20 ml of H₂O. The aqueous fraction was separated and washed once with 1:1 Et₂O: hexane. The combined organic fractions were dried over MgSO₄ and concentrated in vacuo. A solution of the residue in Et₂O was treated with an excess of HCl/Et₂O. A solid precipitate was collected on a filter and recrystallized from MeOH: EtOAc to yield 0.191 g, m.p. 290°–294° C. (11.3%), 0.303 g, m.p. 288°–289° C. (17.9%), 0.429 g, m.p. 288°–289° C. (25.3%), 0.282 g, m.p. 288°–290° C. (16.6%) and 0.365 g, m.p. 285°–288° C. (21.5%) of the titled product.

Step 5: (Procedure C)

A stirred mixture of the product from Step 4 (0.537 g, 2.74 mmol) and EtOAc was mixed with enough aqueous NaHCO₃ to give a solution and the aqueous layer was extracted with EtOAc; the EtOAc extract was dried (MgSO₄) and concentrated. A solution of the residue in -propanol (25 ml) was treated with N-methylmorpholine (0.75 ml, 6.86 mmol) and N-(3- pyridyl)-N'-cyano-O-phenylisourea (see, Example 5 for procedure) (0.98 g, 4.12 mmol) and refluxed under N₂ for 16.75 hours. The cooled reaction mixture was concentrated in vacuo and the residue was chromatographed on silica gel with 1.5% MeOH—0.15% NH₄OH—CH₂Cl₂. The product was crystallized from EtOAc to give 3 which had m.p. 155.5°–157° C.

EXAMPLE 4

(R)-N"-Cyano-N'-(2-hydroxy-1-phenylethyl)-N-(3-pyridyl)guanidine (4).

A stirred mixture of N-(3-pyridyl)-N'-cyano-O-phenylisourea (see, Example 5 for procedure) (3.00 g, 0.0126 mol), (R)-2-phenylglycinol (1.9 g, 0.0130 mol), N-methylmorpholine (30 mL), and isopropanol (20 mL) was refluxed, under nitrogen, for 2 hours; the reaction was complete by TLC with 10% MeOH-CHCl₃. The mixture was concentrated and the residue was chromatographed on silica gel with 1–6% MeOH-CHCl₃. The first product eluted from the column was crystallized from MeOH-EtOAc to give 261 mg of (R)-4, 5-dihydro-4-phenyl-2-(3-pyridyl)aminooxadiazole: mp 125°–130° C.

The second product eluted from the column was crystallized from MeOH-EtOAc-hexane to give 0.32 g of product: mp 175°–176 ° C.

EXAMPLE 5

N"-Cyano-N-(3-pyridyl)-N'-(1-(3-chlorophenyl))propylguanidine (5).

Step 1: 1-(3-Chlorophenyl)propylamine.

A stirred mixture of 3'-chloropropiophenone (5.00 g, 0.0297 mL), 98% formamide (4.6 mL) and formic acid (0.35 mL) in a flask equipped with a thermometer and a reflux condenser with a side arm for removing condensate was warmed at 180°–194 ° C. for 5 hours. Solid that was collected in the condenser was washed into the reaction mixture periodically with formic acid. Distillate and excess formic acid was periodically removed to maintain the internal temperature. At the end of the reaction the cooled mixture was extracted with toluene. The extract was washed with water and brine, dried (MgSO₄) and concentrated to give a crystalline solid (4.28 g). This was refluxed in 2.24 mL of concentrated HCl for 2 hours. The cooled mixture was dissolved in water and washed with EtOAc. The aqueous layer was made alkaline with 50% NaOH and extracted with CHCl₃. The extract was washed with water, dried (MgSO₄) and concentrated to give 3.33 g of 1-(3-chlorophenyl)propylamine.

Step 2: N-(3-Pyridyl)-N'-cyano-O-phenylisourea.

A stirred mixture of diphenyl cyanocarbonimidate (30.0 g, 0.126 mol), 3-aminopyridine (11.9 g, 0.126 mol) and Et20 (320 mL) was kept, under nitrogen, for 4 days. The solid was collected by filtration, washed with Et,20 and dried to give 27.5 g of product. Recrystallization of this material from MeOH-EtOAc-hexane gave N-(3-pyridyl)-N'-cyano-O-phenylisourea: m.p. 154°–155° C.

Step 3: According to Procedure B, a stirred mixture of N-(3-pyridyl)-N'-cyano-O-phenylisourea (Step 2) (3.00 g, 0.0126 mol), 1-(3-chlorophenyl)propylamine (2.35 g, 0.0139 mol), N-methylmorpholine (30 mL) and isopropanol (20 mL) was refluxed, under nitrogen, for 2.5 hours. The product was purified by silica gel chromatography with 1% to 3% MeOH-CHCl₃ and crystallized from MeOH-EtOAc-hexane to give the product: mp 153°–155 ° C.

EXAMPLE 6

N"-Cyano-N-(3-pyridyl)-N'-(1-phenyl)cyclobutylguanidine (6).

According to Procedure B, a stirred mixture of N-(3-pyridyl)-N'-cyano-O-phenylisourea (see, Example 5 for procedure) (3.00 g, 0.0126 mol), 1-phenylcyclobutylamine (2.04 g, 0.0139 mol) (A. Kalir and Z. Pelah, Israel J. Chem. 5:223 (1967)), N-methylmorpholine (30 mL) and isopropanol (20 mL) was refluxed for 5 hours. The product was purified by silica gel chromatography with 1% to 4% MeOH-CHCl₃ to give product which crystallized from MeOH-EtOAc-hexane as an ethyl acetate solvate, mp 159°–160 ° C.

EXAMPLE 7

N"-Cyano-N-(3-pyridyl)-N'-(1-phenyl)ethylguanidine (7).

A mixture of the (R) enantiomer from Example 1 (0.500 g) and the (S) enantiomer of Example 8 as shown in Table I (0.500 g) was dissolved in MeOH and crystallized from MeOH—CH₂Cl₂—(CH₃)₂CO to give 0.550 g of the product: mp 181°–182° C.; $[\alpha]_D^{24}$ 0° (c 0.964, EtOH); IR (Nujol) 3205, 3085, 3060, 3028, 2175, 1590, 1582 cm⁻¹; MS m/z (relative intensity) 265 (M⁺, 54.5), 250 (8.4), 160 (4.2), 146 (13.5), 120 (27.0), 105 (100).

EXAMPLE 8 (COMPOUND 41)

N"-Cyano-N-(3-pyridyl)-N'[1-(3-iodophenyl)ethyl]guanidine.

Step 1: N"-Cyano-N-(3-pyridyl)-N'- [1-[3-(trimethylstannyl)phenyl]ethyl]guanidine.

To a stirred mixture of Compound 39 (0.72 g, 2.0 mmol) and 100 ml of dry dioxane, under nitrogen, was added 0.8 g (2.44 mmol) of hexamethylditin followed by 0.14 g (0.12 mmol) of tetrakis(triphenylphosphine) Pd(0). This mixture was heated to reflux over 80 minutes and at refluxed for 2 hours. The reaction was complete according to thin layer chromatography on silica gel (TLC) (10% MeOH/CHCl₃). The mixture was allowed to cool to room temperature when it was diluted with CH₂Cl₂ and filtered through a pad of celite. The filtrate was concentrated and the residue was crystallized from methyl t-butyl ether to give 0.55 g (62.5%) of the titled product, m.p. 85°–86° C.

Step 2: A solution of the product from Step 1 (0.55 g, 1.53 mmol) in 8 ml of CHCl₃, under nitrogen, was treated (titrated) with 0.1% 12 in CHCl₃ until the peach color persisted (about 12 ml). The mixture was diluted with CHCl₃ and washed with 10% aqueous sodium thiosulfate; the aqueous solution was extracted twice more with CHCl₃. The extracts were washed with water and then with brine. The pooled extract was dried (MgSO₄) and concentrated to give, after crystallization from CH₃CN, 0.368 g (60%), m.p. 174°–176° C. (s170) of the titled product.

EXAMPLE 9 (COMPOUND 44)

(R)-N-(6-Amino-3-pyridyl)-N"-cyano-N'-(1-phenylpropyl)guanidine.

Step 1: 2,5-Diaminopyridine.

A mixture of 10 g (0.0719 mol) of 2-amino-5-nitropyridine and 1 g of 10% Pd/C in 135 ml of EtOH was hydrogenated on the Parr Apparatus with an initial hydrogen pressure of 42 psi. After shaking overnight, an uptake of 17.5 psi was realized (theoretical, 19). The TLC (0.5% NH₄OH/8% MeOH/CHCl₃) showed no starting material. The catalyst was filtered off through a pad of celite and the filtrate was concentrated to give the titled product, a purple solid. This was used in the next step without purification.

Step 2: N'-Cyano-N-(6-amino-3-pyridyl)-O-phenylisourea.

To a stirred mixture of the crude 2,5-diaminopyridine from Step 1 (0.0719 mol) and 100 ml of ethylene glycol dimethylether, under nitrogen, was added diphenylcyanocarbonimidate (17.1 g, 0.0718 mol) in one portion. This mixture was stirred at room temperature for 5 hours and concentrated in vacuo. The residue was triturated three times with Et₂O. The solid residue (17.5 g) was stored under nitrogen until it was chromatographed in two portions: 5.0 g was chromatographed over 1000 ml of silica gel (230–400 mesh) by gravity elution with 5% MeOH/CHCl₃ at a rate of 21 ml/minute to give 3.02 g of product; the other 12.5 g was chromatographed over 1000 ml of silica gel in the same manner (a poorer separation resulted at this loading) to give 7.31 g of product. The two lots were combined and crystallized from CH₃CN to give 8.32 g (45.8%), m.p. 191°–192.5° C. of the titled product as amber needles. (An additional 0.98 g (5.4%) of dark amber needles was also obtained.)

Step 3 (Procedure D): A stirred mixture of the product from Step 2 (1.00 g, 0.00395 mol), (R)-(+)-1-phenylpropylamine (0.583 g, 0.00432 mol), N-methylmorpholine (1.08 ml, 0.0100 mol) and dioxane (20 ml) was refluxed, under nitrogen, for 22 hours and concentrated in vacuo. The residue was triturated with Et₂O to give a solid product that was collected by filtration and washed with Et₂O. It was recrystallized from acetonitrile to give 0.65 g (56%) of the titled product, m.p. 177.5°–178.5° C.

EXAMPLE 10 (Compound 45)

N'-[1-(3-Chlorophenyl)cyclobutyl]-N"-cyano-N-(3-pyridyl)guanidine.

Step 1: 1-(3-chlorophenyl)cyclobutane carbonitrile.

According to the procedure of Butler and Pollatz (Butler, D. E. and J. C. Pollatz, J. Org. Chem. 36:1308 (1971), a reaction flask fitted with a mechanical stirrer, pressure equalizing addition funnel and thermometer was charged, under nitrogen, with 162 ml of DMSO; 17.62 g (0.44 mol) of 60% NaH/oil dispersion was added in portions over 5 minutes. A 20° C. water bath was applied while a solution of 24.5 g (0.162 mol) of (3-chlorophenyl)acetonitrile and 35.9 g (0.195 mol) of 1,3-dibromopropane in Et₂O (100 ml) was added during 75 minutes with good stirring at such a rate that the reaction temperature was kept below 33° C. The mixture was stirred at 20° C. for 2 hours when it was cooled in an ice bath and treated cautiously with 8 ml of 2-propanol. The mixture was stirred at 10° C. for 15 minutes when it was treated cautiously with 120 ml of H20 at such a rate that the reaction temperature was kept below 15° C. After 15 minutes, the layers were separated and the aqueous layer was extracted with 4 portions of Et₂O. The extracts were combined with the organic layer and this mixture was dried (MgSO₄) and concentrated. A red oil was separated from the mineral oil and distilled to give 15.8 g (51%) of the titled product, b.p. 106°–110° C. (0.9 mm Hg).

Step 2: 1-(3-Chlorophenyl))cyclobutanecarboxylic Acid.

According to a modification in the procedure of Kalir and Pelah (see Example 6), a stirred mixture of 12.2 g (0.0637 mol) of the product from Step 1 and powdered KOH (12.8 g, 0.228 mol) in 150 ml of ethylene glycol was heated at 150° C. for 4.5 hours. The mixture was allowed to cool; it was poured into ice-water and treated with cold 6N HCl to a pH of 3. Nitrogen was bubbled through the mixture; a solid formed that was collected, washed well with cold water and dried in vacuo to give 11.16 g of the titled product. This was recrystallized from hexane to give 8.936 g (66.7%), m.p. 102°–104° C; 0.926 g (7%), m.p. 104°–105° C and 0.83 g (6.2%), m.p. 100°–102° C.

Step 3: 1-(3-chlorophenyl)-1-(2,2,2-trichloroethoxycarbonylamino)cyclobutane.

According to the procedure of Ninomiya et al. (Ninomiya, K., Shioiri, T., and S. Yamada, Tetrahedron 30:2151 (1974)), a mixture of the product from Step 2 (1.4 g, 6.65 mmol), diphenylphosphorylazide (2.10 ml, 9.63 mmol) and 1.25 ml (8.95 mmol) of triethyl amine was stirred for 15 minutes and then heated to 71° C. over 60 minutes; 2,2,2-trichloroethanol (0.925 ml, 0.00962 mol) was then added and the mixture was heated at 95° C. for 20 hours and at reflux for 4 hours. The mixture was concentrated and the residue chromatographed over 200 ml of silica gel (230°–400 mesh) by gravity elution with 75% CH₂Cl₂/Hexane to give 2.07 g (87.4%) of the titled product.

Step 4: 1-(3-Chlorophenyl)cyclobutane amine.

According to the procedure of Just and Grozinger (Just, G. and K. Grozinger, Synthesis 457 (1976)), a rapidly stirring mixture of 1.0 ml of 1M potassium dihydrogenphosphate and Zn powder (1.0 g) was treated dropwise during 1 minute with a solution of the product from Step 3 in 5 ml of THF. After 10 minutes, an exotherm to 28° C. was produced and the two-phase system gave way to a slurry. This mixture was stirred for 1 hour when it was filtered through celite; the filter cake was washed alternately with THF and H₂O (twice each). The pooled filtrate was concentrated in vacuo and the aqueous residue was cooled and brought to pH 12–13 with 8% aqueous NaOH. This was extracted 3 times with CHCl$_3$; the extracts were washed with H$_2$O and then with brine. The pooled extract was dried (MgSO$_4$) and concentrated to give 0.23 g (92%) of the titled product.

Step 5: A stirred mixture of N-(3-pyridyl)-N'-cyano-O-phenylisourea (see, Example 5 for procedure) (2.62 g, 0.0110 mol), the product from Step 4 (2.00 g, 0.0110 mol), N-methylmorpholine (3.00 ml, 0.275 mol) and 1,4-dioxane (40 ml) was refluxed, under nitrogen for 4 hours and kept ambient temperature for 1 hour. The product which had precipitated from the mixture was collected by filtration, washed with tert-butyl methyl ether and crystallized from CH3CN to give 1.65 g (46%) of the titled product, m.p. 201°–202° C.

EXAMPLE 11 (COMPOUND 53)

(R)-N"-Cyano-N'-(1-phenylpropyl)-N-[6-(dimethylamino)-3-pyridyl]guanidine.

Step 1: 2-Dimethylamino-5-nitropyridine.

A mechanically stirred mixture of 2-chloro-5-nitropyridine (56.25 g, 0.355 mol) and absolute EtOH (960 ml), under nitrogen was treated, during 15 minutes with 25% aqueous trimethylamine (217 g). The mixture warmed to 40° C. and a thick yellow precipitate formed; it was warmed to 80° C. during 1 hour, cooled to ambient temperature and filtered. The solid was washed with cold 20% H$_2$O-EtOH and dried to give 53.2 g of the titled product, m.p. 151°–152° C.

Step 2: 3-Amino-6-(dimethylamino)pyridine.

A stirred mixture of the product from Step 1 (7.70 g, 0.0461 mol) and stannous chloride dihydrate (56.4 g, 0.250 mol) in absolute EtOH (100 ml) was warmed to 80° C. during 15 minutes and kept at that temperature for 35 minutes. The resulting mixture was kept at ambient temperature for 1 hour, poured onto ice (400 ml) and mixed with NaHCO$_3$ (15 g). It was adjusted to a pH of 8–9 with saturated aqueous NaHCO$_3$ and extracted with EtOAc; the extract was washed with water and brine dried (MgSO4) and concentrated to give 5.98 g of crude product. Pan of this was purified by silica gel chromatography, with 5% MeOH—0.25% NH$_4$OH—CHCl$_3$ to give the titled product.

Step 3: 3-Amino-6-(dimethylamino)pyridine by catalytic reduction of the product from Step 1.

A mixture of 5.0 g (0.03 mol) of 2-dimethylamino-5-nitropyridine and 0.5 g of 85% PtO$_2$ in 150 ml of EtOH was hydrogenated on the Parr Apparatus at an initial hydrogen pressure of 34 psi for 90 minutes. The catalyst was filtered off over celite. The filter cake was washed with EtOH and the filtrate concentrated in vacuo to give the titled product, a purple oil. This was used without further purification in Step 4.

Step 4: N'-Cyano-N-(6-dimethylamino-3-pyridyl)-O-phenylisourea.

A stirred mixture of the crude amine prepared from 5.00 g (0.0299 mol) of the product from Step 1, diphenylcyanocarbonimidate (7.20 g, 0.0302 mol) and ethylene glycol dimethyl ether (60 ml) was kept under nitrogen for 3 hours and diluted with Et20. The solid was collected by filtration, washed with Et$_2$O and dried to give 6.26 g of the titled product.

Step 5: A stirred solution of the product from Step 4 (2.00 g, 0.00711 mol), (R)-(+)-1-phenylpropylamine (1.06 g, 0.00784 mol), N-methylmorpholine (1.69 ml, 0.0154 mol) and isopropanol (13.3 ml) was refluxed, under nitrogen, until the reaction was shown to be complete by TLC (28 hours). It was then concentrated and the residue chromatographed on silica gel with 1 to 4% MeOH-CHCl$_3$. A solution of the product thus obtained in MeOH-EtOAc was decolorized with Darco (activated charcoal) and crystallized from EtOAc-hexane to give 1.02 g, m.p. 109°–111° C. and 0.120 g, m.p. 107°–113° C. of the titled product.

EXAMPLE 12 (COMPOUND 54)

N"-Cyano-N'-(1-phenylpropyl)-N-(3-pyridyl)guanidine, pyridine N-oxide.

According to the procedure of Petersen et al. (Petersen, H. J., Nielsen, C. K. and E. Arrigoni-Martelli, J. Med. Chem. 21:773 (1978)), a stirred mixture of the product from Example 2 (2.00 g, 0.00716 mol) and glacial acetic acid (43.1 ml) was treated, dropwise during 5 minutes, at ambient temperature with 30% hydrogen peroxide (7.62 ml, 0.0672 mol). The mixture was then warmed to 65° C. and kept for 7 hours. The reaction was followed by TLC with 10% MeOH-CHCl$_3$; the starting material had been consumed at this time. The mixture was concentrated in vacuo and the residue was chromatographed on silica gel with mixtures of MeOH-CHCl$_3$ containing from 1 to 6% MeOH. The second compound eluted from the column was crystallized from EtOAc-hexane to give 0.330 g of the titled product, m.p. 187°–188° C.

EXAMPLE 13 (COMPOUND 55)

(R)-N"-Cyano-N'-(1-phenylethyl)-N-(3-pyridyl)guanidine, pyridine N-oxide.

A stirred mixture of the product from Example 1 (2.00 g, 0.00754 mol)) and glacial acetic acid (45.4 ml) was treated dropwise with 30% aqueous H$_2$O$_2$ (8.02 ml) during 5 minutes and then warmed to 65°–70° C. The reaction was followed by TLC with 10% MeOH-CHCl$_3$; the starting material had been consumed after 6 hours. The mixture was concentrated in vacuo; the residue was chromatographed on silica gel with 1–8% MeOH-CHCl$_3$. The second compound eluted from the column was crystallized from MeOH-CH$_3$CN to give 0.180 g of the titled product, m.p. 195°–197° C.

EXAMPLE 14 (COMPOUND 30)

Preparation of Intermediate:
N'-Cyano-N-(6-acetylamino-3-pyridyl)-O-phenylisourea.

Step 1: 2-Acetamido-5-nitropyridine.

To a N$_2$ covered suspension of 3.0 g (21.6 mmol) of 2-amino-5-nitropyridine in 12 ml of CH2C12 was added 9.9 ml (71.2 mmol) of triethylamine followed by 0.13 g (1.1 mmol) of 4-dimethylaminopyridine. The mixture was cooled in an ice bath and there was added 5.06 ml (71.2 mmol) of acetyl chloride dropwise over 18 minutes. The ice bath was removed and after stirring at room temperature for 18 hours, the reaction mixture was diluted with CH$_2$Cl$_2$ and washed once with 20 ml of 1M aqueous K$_2$CO$_3$. The aqueous layer was separated and extracted twice with CH$_2$Cl$_2$. The combined organic fractions were dried over MgSO$_4$ and concentrated in vacuo. The residue was chromatographed over silica gel (20% EtOAc: hexane) and recrystallized from CH$_3$CN to yield 0.653 g, m.p.

196.5°–198° C. (16.7%), 0.157 g, m.p. 183°–193° C. (4.0%) and 0.057 g, m.p. 191°–196° C (1.5%) of the titled product.

Step 2: 2-Acetamido-5-aminopyridine.

A $N_2$ covered solution of 1.19 g (6.6 mmol) of the product from Step 1 in 24 ml of DMF was treated with 2.07 g (32.9 mmol) of ammonium formate followed by 0.36 g of palladium on carbon catalyst. After stirring vigorously at room temperature for 17 hours, the reaction was diluted with MeOH and the catalyst was removed by filtration through celite. The filtrate was concentrated in vacuo and the residue was chromatographed over silica gel (3% MeOH: 0.3% $NH_4OH$: $CH_2Cl_2$) to yield 0.876 g, m.p. 152°–153.5° C. (88.2%) of the titled product.

Step 3: To a $N_2$ covered suspension of 0.909 g (6.0 mmol) of the product from Step 2 in 12 ml of dimethyoxyethane was added 1.43 g of diphenylcyanocarbonimidate. After stirring 16.5 hours at room temperature, the reaction mixture was diluted to a volume of 75 ml with $Et_2O$. A suspended solid was collected on a filter and washed well with $Et_2O$ to yield after drying 1.62 g, m.p. 210.5°–211° C. (91.2%) of the titled product. Procedure C was then followed with the above intermediate to prepare Compound 30, m.p. 193.5°–194.5° C.

EXAMPLE 15 (COMPOUND 34)

Preparation of Intermediate:
N'-Cyano-N-(6-chloro-3-pyridyl)-O-phenylisourea.

A stirred mixture of 5-amino-2-chloropyridine (1.3 g, 0.01 mol) and diphenylcyanocarbonimidate (2.4 g, 0.01 mol) in 15 ml of ethylene glycoldimethyl ether (DME), under nitrogen, was kept at 60° C. for 24 hours and at 85° C. for 6 hours when it was allowed to cool to room temperature. The solvent was removed in vacuo and the residue was heated to a melt at 120° C., under nitrogen, for 1 hour to complete the reaction as shown by TLC (5% $MeOH/CHCl_3$). This was allowed to cool and was triturated with $Et_2O$ to give a solid that was collected by filtration. The solid was washed with $Et_2O$ to give 2.61 g of the titled product.

Procedure C was then followed to prepare Compound 34, m.p. 133°–134° C.

We claim:

1. A compound of Formula I or its pharmaceutically acceptable acid addition salts

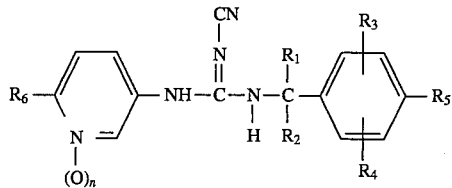

wherein $R_1$ is hydrogen or methyl;

$R_2$ is $C_1$–$C_6$ alkyl, $C_2$–$C_6$ alkenyl, $C_2$–$C_6$ alkynyl, $C_3$–$C_5$ cycloalkyl, $C_3$–$C_5$ cycloalkenyl, hydroxy methyl, methoxy-$C_1$–$C_5$ alkyl, or $R_1$ and $R_2$ are combined to form a $C_3$–$C_6$ carbocyclic ring;

$R_3$ and $R_4$ are each independently selected to be hydrogen, $C_1$–$C_4$ alkyl, F, Cl, Br, I or $CF_3$;

$R_5$ is hydrogen, F or Cl;

$R_6$ is —$NH_2$, —$NHCH_3$, —$NHC_2H_5$, —$NHCH(CH_3)_2$, —$N(CH_3)_2$, —$N(C_2H_5)_2$, $NH(CH_2)_m$—$OC_1$—$C_3$ alkyl (where m is 2 or 3), —$NHC(O)C_1$–$C_3$ alkyl, or except when $R_2$ is a $C_1$–$C_6$ alkyl then $R_6$ is hydrogen Cl or Br; and n is 0 or 1.

2. The compound of claim 1 where $R_1$ and $R_2$ are joined to form cyclobutyl.

3. The compound of claim 1 where $R_1$ is hydrogen and $R_2$ is ethyl.

4. The compound of claim 1 where $R_6$ is $NH_2$, $NHCH_3$ or $NHC_2H_5$.

5. The compound of claim 1 which is
a) (R) N"-Cyano-N-(3-pyridyl)-N'-(1-phenylpropyl)guanidine;
b) N"-Cyano-N-(3-pyridyl)-N'-(1-phenylcyclobutyl)guanidine;
c) N"-Cyano-N-(3-pyridyl)-N'-[1-(3-chlorophenyl)propyl]guanidine;
d) N"-Cyano-N-(3-pyridyl)-N'-phenylcyclopropylmethylguanidine;
e) N"-Cyano-N-(3-pyridyl)-N'- [1-(3 -chlorophenyl)cyclobutyl]guanidine;
f) (R)-N"-Cyano-N-(6-amino-3-pyridyl)-N'-(1-phenylpropyl)guanidine; and
g) N"-Cyano-N-(6-amino-3-pyridyl)-N'-(1-phenylcyclobutyl)guanidine.

6. A method for blocking a potassium channel pathway in living tissue of animals comprising: administering a therapeutically effective amount of compound of Formula I

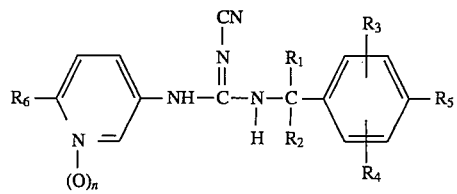

or a pharmaceutically acceptable acid addition salt thereof wherein $R_1$ is hydrogen or methyl:

$R_2$ is $C_1$–$C_6$ alkyl, $C_2$–$C_6$ alkenyl, $C_2$–$C_6$ alkynyl, $C_3$–$C_5$ cycloalkyl, $C_3$–$C_5$ cycloalkenyl, hydroxy methyl, methoxy-$C_1$–$C_5$ alkyl, or $R_1$ and $R_2$ are combined to form a $C_3$–$C_6$ carbocyclic ring;

$R_3$ and $R_4$ are each independently selected to be hydrogen, $C_1$–$C_4$ alkyl, F, Cl, Br, I or $CF_3$;

$R_5$ is hydrogen, F or Cl;

$R_6$ is hydrogen —$NH_2$, —$NHCH_3$, —$NHC_2H_5$, —$NHCH(CH_3)_2$, —$N(CH_3)_2$, —$N(C_2H_5)_2$, $NH(CH_2)_m$—$OC_1$–$C_3$ alkyl (where m is 2 or 3), —$NHC(O)C_1$–$C_3$ alkyl, Cl or Br; and n is 0 or 1;

to an animal in need of such potassium channel blocking.

7. The method of claim 6 wherein the compound of Formula I is administered intravenously, intramuscularly, topically, transdermally, bucally, suppositorally, orally, or parenterally.

8. The method of claim 6 where the compound is administered as a diuretic.

* * * * *